(12) United States Patent
Dowaki et al.

(10) Patent No.: US 10,151,910 B2
(45) Date of Patent: Dec. 11, 2018

(54) IMAGE ANALYSIS USING MICROSCOPE OPTICAL SYSTEM

(71) Applicant: Sony Corporation, Tokyo (JP)

(72) Inventors: Suguru Dowaki, Kanagawa (JP); Eriko Matsui, Tokyo (JP); Hirokazu Tatsuta, Tokyo (JP); Masanobu Tamai, Chiba (JP); Kazuhiro Nakagawa, Saitama (JP)

(73) Assignee: SONY CORPORATION, Tokyo (JP)

( * ) Notice: Subject to any disclaimer, the term of this patent is extended or adjusted under 35 U.S.C. 154(b) by 211 days.

(21) Appl. No.: 14/378,578

(22) PCT Filed: Jan. 21, 2013

(86) PCT No.: PCT/JP2013/000253
§ 371 (c)(1),
(2) Date: Aug. 13, 2014

(87) PCT Pub. No.: WO2013/132734
PCT Pub. Date: Sep. 12, 2013

(65) Prior Publication Data
US 2015/0085098 A1 Mar. 26, 2015

(30) Foreign Application Priority Data
Mar. 7, 2012 (JP) .................. 2012-050152

(51) Int. Cl.
*G02B 21/36* (2006.01)
*G01J 3/44* (2006.01)
(Continued)

(52) U.S. Cl.
CPC .............. *G02B 21/365* (2013.01); *G01J 3/44* (2013.01); *G01N 21/31* (2013.01); *G01N 21/65* (2013.01);
(Continued)

(58) Field of Classification Search
CPC .................................................. G02B 21/365
(Continued)

(56) References Cited

U.S. PATENT DOCUMENTS 5,845,639 A * 12/1998 Hochman ............ A61B 5/0059
356/39
6,002,476 A * 12/1999 Treado ...................... G01J 3/44
356/301

(Continued)

FOREIGN PATENT DOCUMENTS

JP  04-161839  6/1992
JP  05-119035  5/1993
(Continued)

OTHER PUBLICATIONS

Bolwien,C. et.al., "Rapid detection of bacterial contamination in cell or tissue cultures based on Raman spectroscopy", Proceedings of SPIE, vol. 6853, Biomedical Optical Spectroscopy, Mar. 19, 2008, 68530F. (11 Pages).

(Continued)

*Primary Examiner* — Tarifur Chowdhury
*Assistant Examiner* — Omar Nixon
(74) *Attorney, Agent, or Firm* — Chip Law Group

(57) ABSTRACT

An observation apparatus according to the present technology includes a microscope optical system, an imaging unit, a spectroscopic unit, and a detection unit. The imaging unit captures an image via the microscope optical system. The spectroscopic unit acquires an absorption spectrum or a Raman spectrum in an ultraviolet, visible, or infrared area via the microscope optical system. The detection unit detect an observation target object in an observed sample by using the absorption spectrum or the Raman spectrum.

15 Claims, 13 Drawing Sheets

(51) Int. Cl.
- *G01N 21/65* (2006.01)
- *G01N 21/31* (2006.01)
- *G02B 21/16* (2006.01)
- *G01N 21/64* (2006.01)
- *G02B 21/00* (2006.01)

(52) U.S. Cl.
CPC ......... *G02B 21/0096* (2013.01); *G02B 21/16* (2013.01); *G01N 21/6458* (2013.01); *G02B 21/0092* (2013.01)

(58) Field of Classification Search
USPC .......................................................... 356/301
See application file for complete search history.

(56) References Cited

U.S. PATENT DOCUMENTS

| | | | | |
|---|---|---|---|---|
| 2004/0109231 | A1* | 6/2004 | Haisch | A61B 5/0066 359/385 |
| 2006/0001870 | A1* | 1/2006 | Voigt | G01J 3/44 356/301 |
| 2006/0055923 | A1* | 3/2006 | Stewart | G01J 3/44 356/301 |
| 2006/0184037 | A1* | 8/2006 | Ince | A61B 1/042 600/476 |
| 2009/0002702 | A1* | 1/2009 | Maier | A61B 5/417 356/301 |
| 2009/0274360 | A1* | 11/2009 | Suzuki | G01N 21/6428 382/133 |
| 2009/0303582 | A1* | 12/2009 | Karasawa | G02B 21/365 359/363 |
| 2010/0045778 | A1* | 2/2010 | Yelin | H04N 5/2256 348/45 |
| 2010/0251438 | A1* | 9/2010 | Huber | G01N 15/1475 850/1 |
| 2010/0309464 | A1* | 12/2010 | Treado | G01J 3/0218 356/301 |
| 2011/0235034 | A1* | 9/2011 | Fukuda | G01J 3/02 356/319 |
| 2011/0242533 | A1* | 10/2011 | Treado | G01J 3/32 356/326 |
| 2012/0154560 | A1* | 6/2012 | Harding | G01N 21/84 348/61 |

FOREIGN PATENT DOCUMENTS

| | | |
|---|---|---|
| JP | 05-142144 A | 6/1993 |
| JP | 07-270311 | 10/1995 |
| JP | 10-267845 | 10/1998 |
| JP | 2001-215193 A | 8/2001 |
| JP | 2004-514133 A | 5/2004 |
| JP | 2009-065848 | 4/2009 |
| JP | 2009-065848 A | 4/2009 |
| JP | 2010-509601 | 3/2010 |
| JP | 2010-509601 A | 3/2010 |
| JP | 2010-117052 | 10/2010 |
| JP | 2011-096181 A | 5/2011 |
| JP | 2004-535569 | 8/2011 |
| JP | 2011-257691 A | 12/2011 |

OTHER PUBLICATIONS

International Search Report issued in connection with International Patent Application No. PCT/JP2013/000253, dated Feb. 7, 2013. (5 pages).

Office Action for JP Patent Application No. 2014-503431, dated Aug. 30, 2016, 4 pages.

Office Action for JP Patent Application No. 2016-231489, dated Sep. 26, 2017, 5 pages of Office Action and 3 pages of English Translation.

* cited by examiner (a)

(b)

(a)

(b)

IMAGE ANALYSIS USING MICROSCOPE OPTICAL SYSTEM

CROSS REFERENCES TO RELATED APPLICATIONS

The present application is a national stage of International Application No. PCT/JP2013/000253 filed on Jan. 21, 2013 and claims priority to Japanese Patent Application No. 2012-050152 filed on Mar. 7, 2012, the disclosure of which is incorporated herein by reference.

BACKGROUND

The present technology relates to an observation apparatus, an observation program, and an observation method that are capable of observing an observation target object via a microscope optical system.

When a user observes an observation target object via a microscope, the observation target object that the user wants to observe is only a part of an observed sample in many cases, such as a case where the user observes a cell included in a culture solution. In such a case, the user needs to search for the observation target object in the observed sample, which imposes a heavy burden on the user.

Using some analysis method to detect the observation target object in the observed sample is also enabled. For example, with an infrared spectroscopic analyzer disclosed in Patent Document 1, it is possible to determine whether a measurement area contains the observation target object or not based on an infrared spectroscopic spectrum of the measurement area.

Patent Document 1: Japanese Patent Application Laid-open No. Hei 07-270311

SUMMARY

Problem to be Solved by the Invention

However, if the observed sample is transferred between an analysis apparatus and a microscope apparatus, the observation target object is moved in the observed sample, and there is a possibility that the position of the detected observation target object does not have any means. Additionally, the observation target object may be moved or deteriorated with the lapse of time.

In view of the circumstances as described above, it is an object of the present technology to provide an observation apparatus, an observation program, and an observation method that are suitable for the detection and observation of an observation target object.

Means for Solving the Problem

In view of the circumstances as described above, according to an embodiment of the present technology, there is provided an observation apparatus including a microscope optical system, an imaging unit, a spectroscopic unit, and a detection unit.

The imaging unit captures an image via the microscope optical system.

The spectroscopic unit acquires an absorption spectrum or a Raman spectrum in an ultraviolet, visible, or infrared area via the microscope optical system.

The detection unit detects an observation target object in an observed sample by using the absorption spectrum or the Raman spectrum.

According to this configuration, since the spectroscopic unit and the imaging unit use the common microscope optical system, a relative positional relationship between a position at which the spectroscopic unit acquires the absorption spectrum or the Raman spectrum and a field of view of the imaging unit is defined. For that reason, the imaging unit can capture an image of the observation target object by using position information of the observation target object, which is detected by the detection unit based on the absorption spectrum or the Raman spectrum. This can eliminate the necessity for a user to search for the observation target object by him/herself and allows the user to easily capture a microscope image of the observation target object.

The observation apparatus may further include a control unit to cause the imaging unit to capture an image of the observation target object detected by the detection unit.

According to this configuration, the control unit controls the microscope optical system, illumination, and the like to acquire an image of the observation target object detected by the detection unit, and thus the detection and imaging of the observation target object can be automated.

The detection unit may detect an observation target object candidate based on an image of the observed sample, the image being captured by the imaging unit, and may determine whether the observation target object candidate is the observation target object or not by using the absorption spectrum or the Raman spectrum.

According to this configuration, the detection unit only needs to perform the determination by the absorption spectrum or the Raman spectrum on the observation target object candidate detected by using, for example, a pixel value, previously based on the image of the observed sample. This allows the observation target object to be detected fast.

The detection unit may detect the observation target object for each predetermined time, and the control unit may cause the imaging unit to capture an image of the observation target object detected by the detection unit for each predetermined time.

According to this configuration, also when the observation target object is moved with the lapse of time, the detection unit can track the observation target object. This allows the observation of the observation target object over a predetermined period of time (time-lapse observation).

The detection unit may determine a state of the observation target object based on the image captured by the imaging unit or the absorption spectrum or the Raman spectrum acquired by the spectroscopic unit, for each predetermined time, and may determine whether the observation target object is an observation target or not.

According to this configuration, in the case where the observation target object enters a state that is not suitable for the observation with the lapse of time, the observation can be terminated.

In view of the circumstances as described above, according to an embodiment of the present technology, there is provided an observation program including a detection unit and a control unit.

The detection unit detects an observation target object in an observed sample by using an absorption spectrum or a Raman spectrum in an ultraviolet, visible, or infrared area, the absorption spectrum or the Raman spectrum being acquired by a spectroscopic unit via a microscope optical system.

The control unit causes an imaging unit to capture an image of the observation target object detected by the detection unit.

In view of the circumstances as described above, according to an embodiment of the present technology, there is provided an observation method including: detecting, by a detection unit, an observation target object in an observed sample by using an absorption spectrum or a Raman spectrum in an ultraviolet, visible, or infrared area, the absorption spectrum or the Raman spectrum being acquired by a spectroscopic unit via a microscope optical system; and causing, by a control unit, an imaging unit to capture an image of the observation target object detected by the detection unit.

In view of the circumstances as described above, according to another embodiment of the present technology, there is provided an observation apparatus including a microscope optical system, an imaging unit, an ultraviolet/visible/infrared spectroscopic unit, and a Raman spectroscopic unit.

The imaging unit captures an image via the microscope optical system.

The ultraviolet/visible/infrared spectroscopic unit acquires an absorption spectrum in an ultraviolet, visible, or infrared area via the microscope optical system.

The Raman spectroscopic unit acquires a Raman spectrum via the microscope optical system.

Effect of the Invention

As described above, according to the present technology, it is possible to provide an observation apparatus, an observation program, and an observation method that are suitable for the detection and observation of an observation target object.

Additional features and advantages are described herein, and will be apparent from the following Detailed Description and the figures.

DETAILED DESCRIPTION

Figure 1:
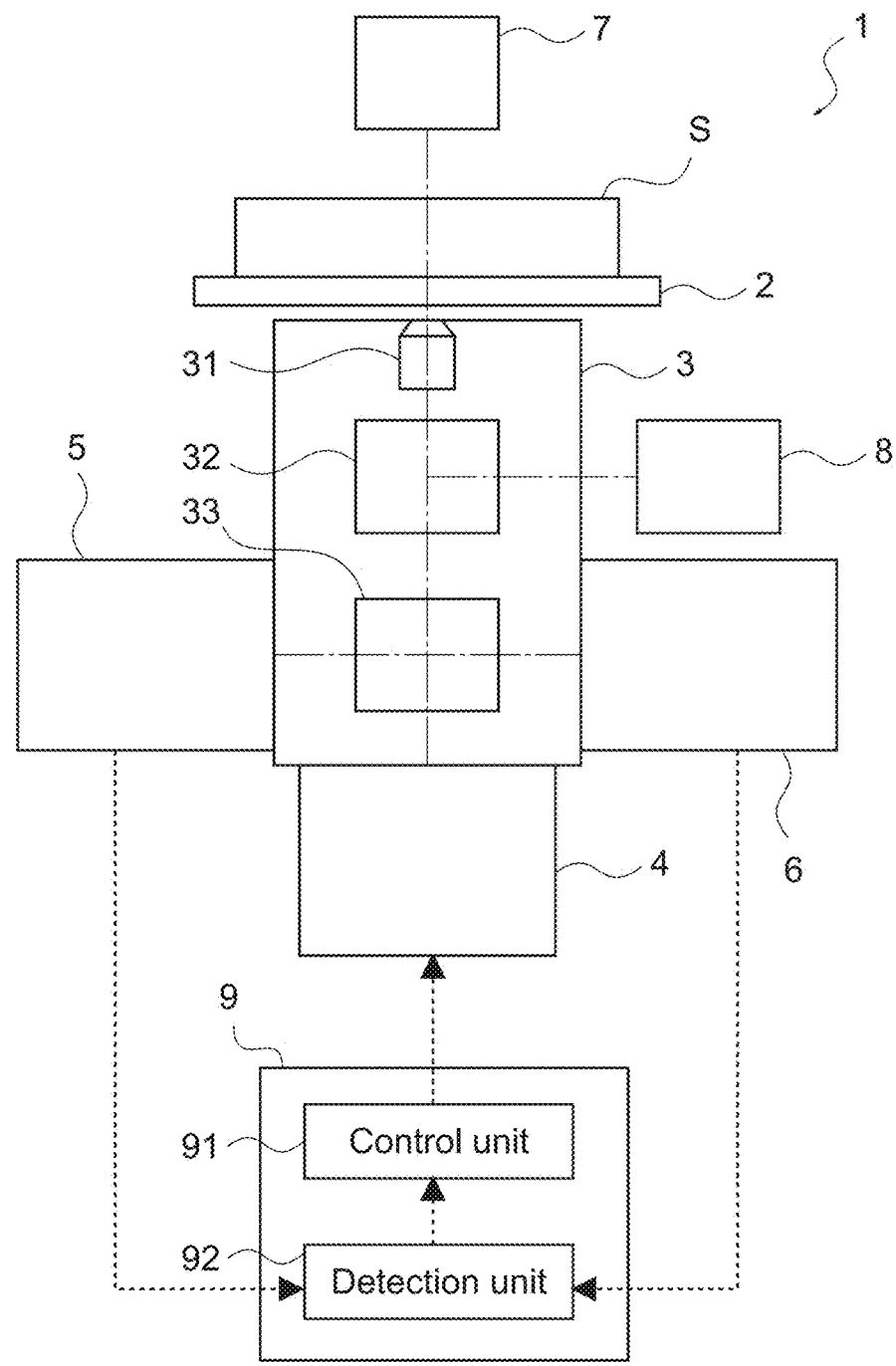
FIG. 1 is a schematic diagram showing a configuration of an observation apparatus according to an embodiment of the present technology.

Description will be given on an observation apparatus according to this embodiment. FIG. 1 is a schematic diagram showing a configuration of an observation apparatus 1 according to this embodiment. As shown in FIG. 1, the observation apparatus 1 includes a stage 2, a microscope optical system 3, an imaging unit 4, an ultraviolet/visible/infrared spectroscopic unit 5, a Raman spectroscopic unit 6, a transillumination unit 7, a epi-illumination unit 8, and a control unit 9. Further, an incubator S for accommodating an observed sample is placed on the stage 2.

The microscope optical system 3 is disposed to face the stage 2. The imaging unit 4, the ultraviolet/visible/infrared spectroscopic unit 5, the Raman spectroscopic unit 6, and the epi-illumination unit 8 are connected to the microscope optical system 3. The transillumination unit 7 is disposed on the opposite side of the microscope optical system 3 with respect to the stage 2. The control unit 9 is connected to the imaging unit 4, the ultraviolet/visible/infrared spectroscopic unit 5, and the Raman spectroscopic unit 6 and also connected to the units such as the stage 2 and the microscope optical system 3 as needed.

The stage 2 supports the incubator S and defines a relative distance between the incubator S and the microscope optical system 3. The stage 2 can be configured to be movable in a horizontal direction (X-Y direction) and a vertical direction (Z direction) by a drive source such as a motor. It should be noted that instead of the stage 2, the microscope optical system 3 may be configured to be movable with respect to the stage 2.

The incubator S accommodates a dish or a well plate in which an observation target object (cells or the like) is cultured, and is configured to allow various observations while maintaining a culture environment, that is, keeping cells alive. In the incubator S, its lid is opened and closed many times in the case of a medium replacement or the addition of a medical agent (cytokine or the like), or in the case where a reaction of cells to the medical agent is observed. In the case where the maintenance of the culture environment is affected, it is desirable to cover the whole of the observation apparatus 1 to maintain the culture environment. Further, the incubator S may be configured to automate the medium replacement or the addition of a test reagent.

The microscope optical system 3 guides light (containing ultraviolet rays and infrared rays), which has penetrated through the observed sample or has been generated in the observed sample, to the ultraviolet/visible/infrared spectroscopic unit 5, the Raman spectroscopic unit 6, and the imaging unit 4. Although the detailed configuration of the microscope optical system 3 will be described later, the ultraviolet/visible/infrared spectroscopic unit 5 acquires an absorption spectrum of the observed sample via the microscope optical system 3, and the Raman spectroscopic unit 6 acquires a Raman spectrum of the observed sample via the microscope optical system 3. The imaging unit 4 acquires a microscope image of the observed sample via the microscope optical system 3.

The imaging unit 4 captures a microscope image of the observed sample by the microscope optical system 3. The imaging unit 4 includes an imaging device such as a CCD (Charge Coupled Device) image sensor or a CMOS (Complementary Metal Oxide Semiconductor) image sensor and is configured to be capable of capturing a still image or a moving image of the observed sample. The imaging unit 4 can capture all or at least one of a bright-field image, a dark-field image, a phase difference image, a fluorescent image, a polarizing microscope image, and the like of the observed sample in accordance with the configuration of the microscope optical system 3, the transillumination unit 7, or the like. The imaging unit 4 outputs the captured image to the control unit 9, another information processing apparatus not shown in the figure, or the like.

The ultraviolet/visible/infrared spectroscopic unit 5 generates a two-dimensional spectroscopic image in an ultraviolet, visible, or infrared area of the observed sample via the microscope optical system 3 and acquires an absorption spectrum (ultraviolet/visible/infrared spectroscopic spectrum) in the ultraviolet, visible, or infrared area from the two-dimensional spectroscopic image.

The ultraviolet, visible, or infrared light that has exited from the transillumination unit 7 penetrates through the observed sample and is guided to the ultraviolet/visible/infrared spectroscopic unit 5 by the microscope optical system 3, and thus a two-dimensional spectroscopic image is generated. In the generated two-dimensional spectroscopic image, the ultraviolet/visible/infrared spectroscopic unit 5 extracts a flat transmission spectrum of an area where the observation target object does not exist, and subsequently obtains a common logarithm of a ratio of the transmission spectrum to a transmission spectrum of each pixel, which allows the acquisition of an absorption spectrum. The ultraviolet/visible/infrared spectroscopic spectrum (see FIG. 3) represents plots of absorbance with respect to the wavelength of the ultraviolet, visible, or infrared light that has penetrated through the observed sample, and contains information on the characteristics of the observed sample (molecular structure or chemical state).

It should be noted that the ultraviolet/visible/infrared spectroscopic unit 5 may be any unit as long as the absorption spectrum can be acquired in at least one of the ultraviolet, visible, and infrared areas, or all areas of the ultraviolet, visible, and infrared areas. Further, the ultraviolet/visible/infrared spectroscopic unit 5 can perform fluorescent labeling on the observed sample in advance and thus acquire an ultraviolet/visible/infrared spectroscopic spectrum of the fluorescence. The ultraviolet/visible/infrared spectroscopic unit 5 outputs the acquired absorption spectrum to the control unit 9.

The Raman spectroscopic unit 6 generates a two-dimensional spectroscopic image of Raman scattering of the observed sample via the microscope optical system 3. The Raman spectroscopic unit 6 acquires a spectrum of the Raman scattering (Raman spectrum) from the two-dimensional spectroscopic image. The Raman spectroscopic unit 6 applies excitation light (laser light) having a specific wavelength to the observed sample via the microscope optical system 3. The light emitted from the observed sample accordingly (hereinafter, referred to as emitted light) is guided to the Raman spectroscopic unit 6 via the microscope optical system 3 and an image is captured.

In the generated two-dimensional spectroscopic image, the Raman spectroscopic unit 6 extracts a flat spectrum of an area where the observation target object does not exist, and subsequently obtains a difference between the spectrum and a spectrum of each pixel, which allows the acquisition of a Raman spectrum of the observation target object itself. The Raman spectrum (see FIG. 5) represents plots of the intensity of emitted light with respect to the wavelength. The emitted light contains scattered light by Raman scattering, and the wavelength transition (Raman shift) of the scattered light by Raman scattering differs depending on the characteristics of the observed sample (molecular structure or crystalline structure), that is, the Raman spectrum contains information on the characteristics of the observed sample. The Raman spectroscopic unit 6 outputs the acquired Raman spectrum to the control unit 9.

The transillumination unit 7 applies illumination light to the observed sample. As described above, the imaging unit 4 is configured to be capable of capturing all or at least one of a bright-field image, a dark-field image, a phase difference image, a fluorescent image, a polarizing microscope image, and the like, and the transillumination unit 7 is configured to be capable of applying illumination, which corresponds to an image to be captured, to the observed sample.

Specifically, the transillumination unit 7 applies normal white light to the observed sample in the case where the imaging target of the imaging unit 4 is a bright-field image, and applies illumination light to the observed sample, the illumination light having a numerical aperture component larger than the numerical aperture (NA) of an objective lens, in the case where the imaging target of the imaging unit 4 is a dark-field image. Further, in the case where the imaging target of the imaging unit 4 is a phase difference image, the transillumination unit 7 applies illumination light to the observed sample via a ring aperture selected in accordance with the objective lens. For the transillumination unit 7, a device whose configuration can be automatically switched by the control unit 9 is suitable so as to appropriately apply optimum illumination light in accordance with such various imaging techniques or imaging magnifications.

The epi-illumination unit 8 applies various types of illumination light to the observed sample via the microscope optical system 3. The epi-illumination unit 8 can operate with respect to the transillumination unit 7 supplementarily or alternatively and can be provided as needed.

The control unit 9 controls the units of the observation apparatus 1, such as the stage 2 and the microscope optical system 3, based on the output of the ultraviolet/visible/infrared spectroscopic unit 5 or the Raman spectroscopic unit 6, and captures a microscope image of the observed sample in the imaging unit 4. The control unit 9 is an information processing apparatus such as a PC (Personal computer) and includes a detection unit 91 and a control unit 92 as functional configurations.

The detection unit 91 detects the observation target object in the observed sample by any one of the absorption spectrum acquired by the ultraviolet/visible/infrared spectroscopic unit 5 or the Raman spectrum acquired by the Raman spectroscopic unit 6. The observation target object is, for example, a cell or the mass of cells and is contained in the observed sample accommodated in the incubator S.

The detection unit 91 can determine, by the analysis of the absorption spectrum or the Raman spectrum, whether there is an observation target object or not at a position where the absorption spectrum or the Raman spectrum is acquired by the ultraviolet/visible/infrared spectroscopic unit 5 or the Raman spectroscopic unit 6. In other words, the detection unit 91 can detect the observation target object in the observed sample by two- or three-dimensionally scanning the position where the absorption spectrum or the Raman spectrum is acquired. The method of detecting the observation target object by the detection unit 91 will be described later.

The control unit 92 causes the imaging unit 4 to capture an image of the observation target object in the observed sample, the observation target object being detected by the detection unit 91. Specifically, the control unit 92 can control the relative positions of the stage 2 and the microscope optical system 3 such that the observation target object is included in the imaging range of the imaging unit 4, and control the imaging magnification of the microscope optical system 3 and an illumination timing of the transillumination unit 7 or the like as well as instructs the imaging unit 4 to capture an image.

[Configuration of Microscope Optical System]

The configuration of the microscope optical system 3 will be described. As shown in FIG. 1, the microscope optical system 3 can include an objective lens 31, a first optical path switching unit 32, and a second optical path switching unit 33. The objective lens 31 is disposed to face the observed sample (that is, the incubator S). The first optical path switching unit 32 is disposed subsequent to the objective lens 31, and the second optical path switching unit 33 is disposed subsequent to the first optical path switching unit 32.

The objective lens 31 enlarges the light, which has penetrated through the observed sample or has been emitted from the observed sample, to a predetermined enlargement magnification. The objective lens 31 can be configured to be switchable in accordance with the imaging techniques or imaging magnifications of the bright-field image, the dark-field image, the phase difference image, the fluorescent image, the polarizing microscope image, and the like.

The first optical path switching unit 32 switches the optical path of incident light from the objective lens 31. Specifically, in the case where the epi-illumination unit 8 illuminates the observed sample, the first optical path switching unit 32 can serve as a half mirror and thus can reflect the illumination light from the epi-illumination unit 8 toward the objective lens while transmitting the incident light from the objective lens 31 toward the second optical path switching unit 33.

Further, in the case where the fluorescence of the observed sample is observed by the imaging unit 4 or the ultraviolet/visible/infrared spectroscopic unit 5, the first optical path switching unit 32 can serve as a dichroic mirror. In other words, the wavelength band of the excitation light applied to the observed sample from the epi-illumination unit 8 is cut by the dichroic mirror, and only the wavelength band of the fluorescence is caused to penetrate toward the second optical path switching unit 33. For the first optical path switching unit 32, a device that is switchable as needed is suitable. Alternatively, the first optical path switching unit 32 may not be provided in the case where such switching of the optical path is unnecessary.

The second optical path switching unit 33 switches the optical path of incident light from the first optical path switching unit 32. The second optical path switching unit 33 can sort the incident light into directions of the imaging unit 4, the ultraviolet/visible/infrared spectroscopic unit 5, and the Raman spectroscopic unit 6 at a predetermined proportion. Further, the second optical path switching unit 33 can sort the incident light into any one of or two directions of the imaging unit 4, the ultraviolet/visible/infrared spectroscopic unit 5, and the Raman spectroscopic unit 6 at a predetermined proportion, the directions being used for the observation of the observed sample. For example, in the case where the two-dimensional spectroscopic image in the ultraviolet, visible, or infrared area (or the two-dimensional spectroscopic image of the Raman scattering) is measured, the first optical path switching unit 32 can sort all the incident light into the ultraviolet/visible/infrared spectroscopic unit 5 (or the Raman spectroscopic unit 6), and in the case where the imaging unit 4 captures an image of the observed sample, the first optical path switching unit 32 can sort all the incident light into the imaging unit 4.

In this embodiment, the imaging unit 4, the ultraviolet/visible/infrared spectroscopic unit 5, and the Raman spectroscopic unit 6 use the common optical paths in the microscope optical system 3, but the present technology is not limited to this. In the microscope optical system 3, if the optical paths of the imaging unit 4, the ultraviolet/visible/infrared spectroscopic unit 5, and the Raman spectroscopic unit 6 are provided independently, it is only necessary to specify the relative positional relationship of the respective optical paths. In other words, it is only necessary to define the positional relationship between the field of the two-dimensional spectroscopic image by the ultraviolet/visible/infrared spectroscopic unit 5 or the Raman spectroscopic unit 6 and the field of the imaging unit 4. More specifically, it is only necessary to find out to which position of the field of the imaging unit 4 the existence position of the observation target object corresponds, the observation target object being detected based on the spectrum by the ultraviolet/visible/infrared spectroscopic unit 5 or the Raman spectroscopic unit 6.

The observation apparatus 1 can be configured as described above, but the observation apparatus 1 can have a different configuration as needed. For example, in the case where the polarizing microscope image of the observed sample is captured, it is also possible to provide a polarizer in the transillumination unit 7 and provide an analyzer in the microscope optical system 3.

[Operation of Observation Apparatus]

Figure 2:
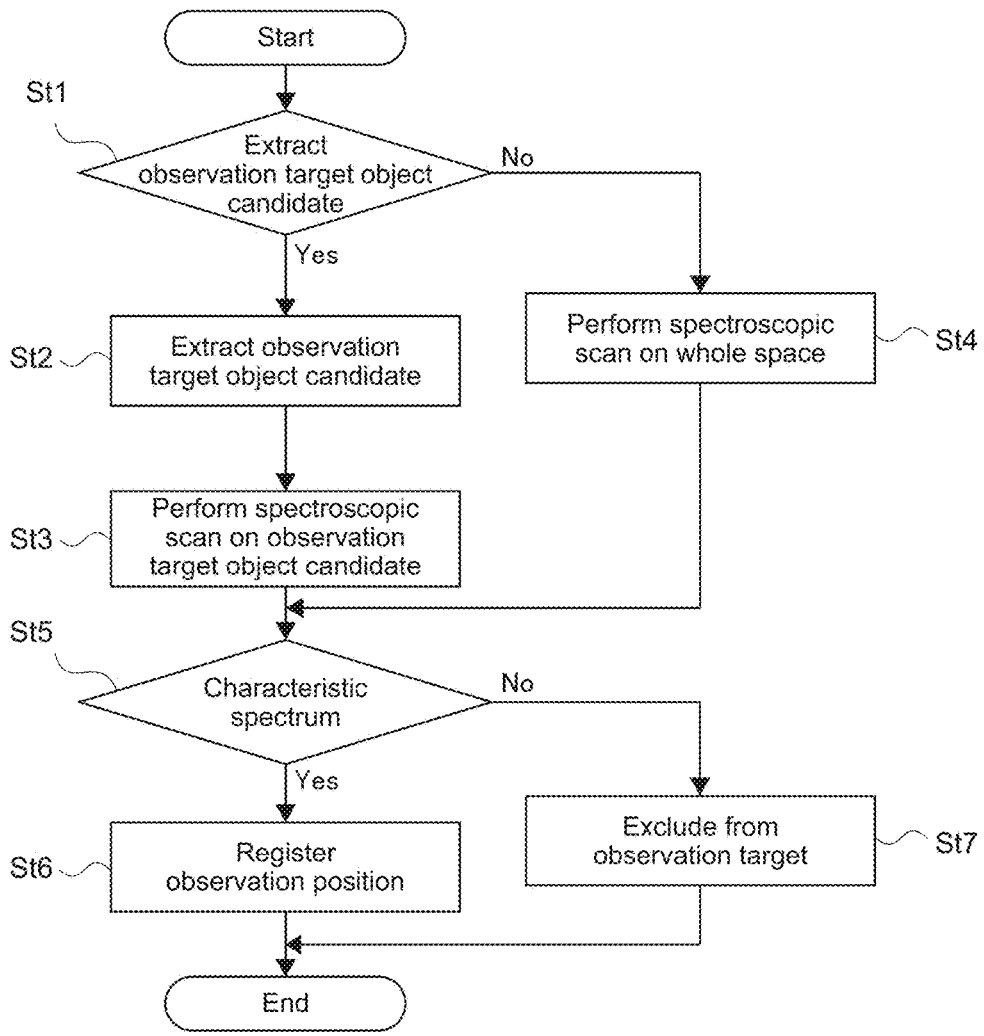
FIG. 2 is a flowchart showing an operation of the observation apparatus.

The operation of the observation apparatus 1 will be described. FIG. 2 is a flowchart showing the operation of the observation apparatus 1. On the stage 2, the incubator S in which the observed sample including the observation target object is accommodated is placed beforehand.

First, whether an observation target object candidate is extracted or not is designated by a user (St1). The user can perform this designation by an operation input to the control unit 9 or the like. For example, the user can select the extraction of an observation target candidate in the case where the amount of the observation target object that exists in the observed sample is small or in the case where the position where the observation target object in the observed sample exists can be specified to some extend beforehand.

In the case where the extraction of the observation target object candidate is selected by the user (St1: Yes), the observation target object candidate is extracted (St2). Specifically, the detection unit 91 performs image processing and the like on an image of the observed sample, the image being captured by the imaging unit 4 at a low magnification (hereinafter, referred to as a low magnification image), and thus the observation target candidate object can be extracted. The detection unit 91 can extract the observation target object candidate based on the difference in pixel value in each predetermined range, for example. Further, the user can extract the observation target object candidate based on the low magnification image. The detection unit 91 or the user can register spatial coordinates (X, Y, Z coordinates) of the observation target object candidate in the control unit 92.

Subsequently, at least one of the ultraviolet/visible/infrared spectroscopic unit 5 and the Raman spectroscopic unit 6 executes a spectroscopic scan on the observation target object candidate (St3). In the case where the spectroscopic scan is executed by the ultraviolet/visible/infrared spectroscopic unit 5, under the control of the control unit 92, illumination light is caused to exit from the transillumination unit 7 to enter the ultraviolet/visible/infrared spectroscopic unit 5 via the microscope optical system 3. In response to this, in the ultraviolet/visible/infrared spectroscopic unit 5, a two-dimensional spectroscopic image in an ultraviolet, visible, or infrared area at the position of the observation target object candidate is captured and an absorption spectrum is acquired. The relative positions of the stage 2 and the microscope optical system 3 can be adjusted by the control unit 92, and adjacent areas of the observation target object candidate can also be scanned. It should be noted that, at that time, a smaller enlargement magnification of the microscope optical system 3 allows a high-speed scan of a broader field of view, which is suitable.

In the case where the spectroscopic scan is executed by the Raman spectroscopic unit 6, under the control of the control unit 92, excitation light is caused to exit from the Raman spectroscopic unit 6 to be applied to the observed sample via the microscope optical system 3. The emitted light (containing the Raman scattering light) from the observed sample enters the Raman spectroscopic unit 6 via the microscope optical system 3. In response to this, in the Raman spectroscopic unit 6, a two-dimensional spectroscopic image of the Raman scattering at the position of the observation target object candidate is captured and a Raman spectrum is acquired. The relative positions of the stage 2 and the microscope optical system 3 can be adjusted by the control unit 92, and adjacent areas of the observation target object candidate can also be scanned. It should be noted that, at that time, a smaller enlargement magnification of the microscope optical system 3 allows a high-speed scan of a broader field of view, which is suitable.

On the other hand, in the case where the extraction of a candidate area where the observation target object exists is not selected by the user (St1: No), a spectroscopic scan is executed for the whole of a space (sample space) in which the observed sample exists (St4). As in the case where the observation target object candidate is extracted (St2), the relative positions of the stage 2 and the microscope optical system 3 can be adjusted by the control unit 92, and adjacent areas of the observation target object candidate can also be scanned.

Subsequently, the detection unit 91 confirms whether the absorption spectrum acquired by the ultraviolet/visible/infrared spectroscopic unit 5 or the Raman spectrum acquired by the Raman spectroscopic unit 6 has a characteristic spectrum or not (St5).

Figure 3:
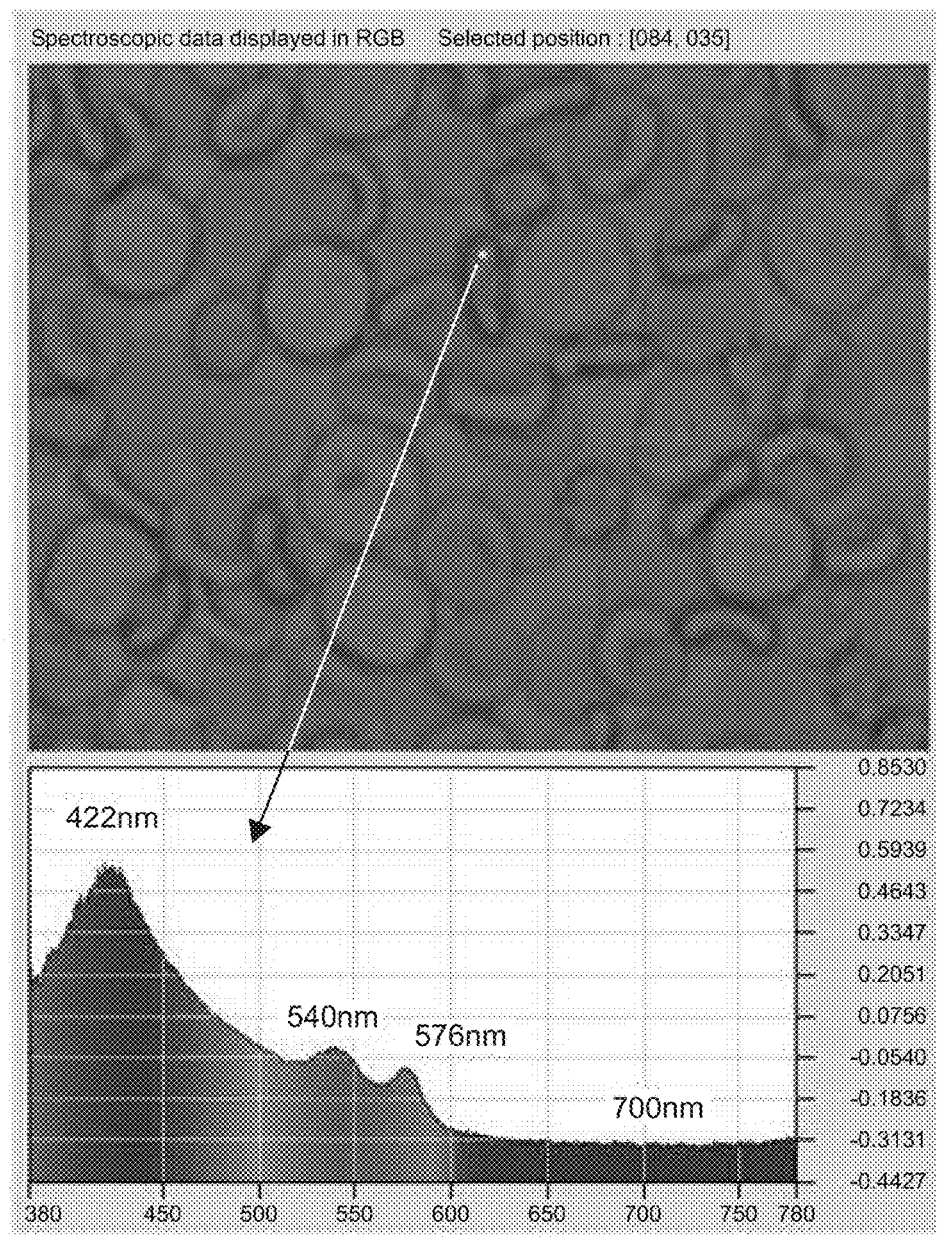
FIG. 3 shows an example of a two-dimensional spectroscopic image of an ultraviolet, visible, or infrared area acquired by an ultraviolet/visible/infrared spectroscopic unit of the same observation apparatus, and an example of an absorption spectrum thereof.
Figure 4:
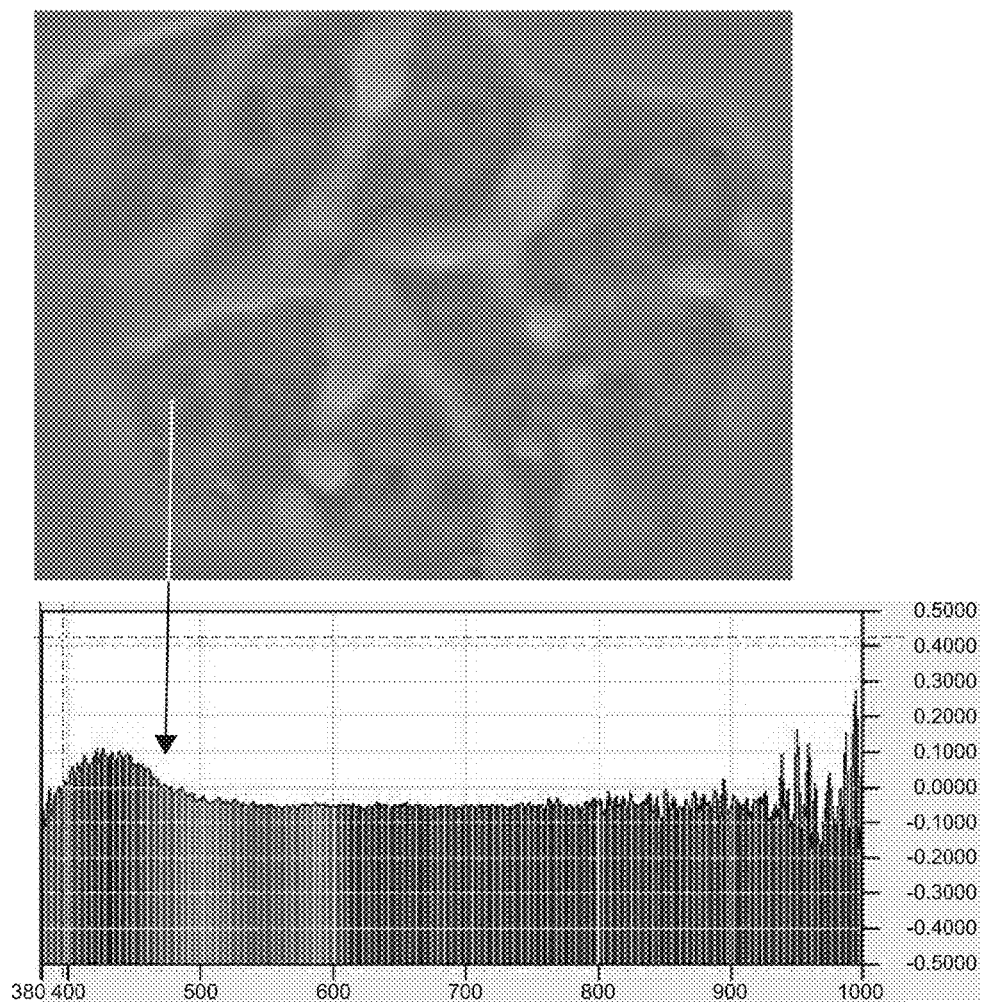
FIG. 4 shows an example of a two-dimensional spectroscopic image of the ultraviolet, visible, or infrared area acquired by the ultraviolet/visible/infrared spectroscopic unit of the same observation apparatus, and an example of an absorption spectrum thereof.

FIGS. 3 and 4 each show an example of the two-dimensional spectroscopic image of the ultraviolet, visible, or infrared area, which is acquired by the ultraviolet/visible/infrared spectroscopic unit 5, and an example of an absorption spectrum at a certain spot of the two-dimensional spectroscopic image. The observation target object in FIG. 3 is red blood cells, and the observation target object in FIG. 4 is HepG2 (human hepatoma cell line).

The absorption spectrum shown in FIG. 3 is generated with a position, at which the observation target object (red blood cells) does not exist, as a reference. As shown in FIG. 3, in the case where the observation target object is red blood cells, in an absorption spectrum of a position at which the red blood cells exist in the two-dimensional spectroscopic image, a strong absorption derived from hemoglobin is recognized in a Soret band of wavelengths ranging approximately from 380 nm to 460 nm. On the other hand, in an absorption spectrum of a position at which the red blood cells do not exist in the two-dimensional spectroscopic image, a strong absorption derived from hemoglobin is not recognized. In other words, in the case where the observation target object is red blood cells, the red blood cells can be detected based on the absorption in the Soret band.

The absorption spectrum shown in FIG. 4 is generated with a position, at which the observation target object (HepG2) does not exist, as a reference. As shown in FIG. 4, in the case where the observation target object is HepG2, in an absorption spectrum of a position at which HepG2 exists in the two-dimensional spectroscopic image, a strong absorption derived from heme included in a vesicle membrane or the like in a cell is recognized in the Soret band. On the other hand, in an absorption spectrum of a position at which HepG2 does not exist in the two-dimensional spectroscopic image, a strong absorption derived from that component is not recognized. In other words, in the case where the observation target object is HepG2, HePG2 can be detected based on the absorption in the wavelengths ranging from 400 nm to 480 nm.

In addition to this, the detection unit 91 can detect the observation target object based on the absorption spectrum peculiar to the observation target object. The observation target object detectable by the absorption spectrum is not limited to cells and only needs to have a characteristic absorption spectrum.

Figure 5:
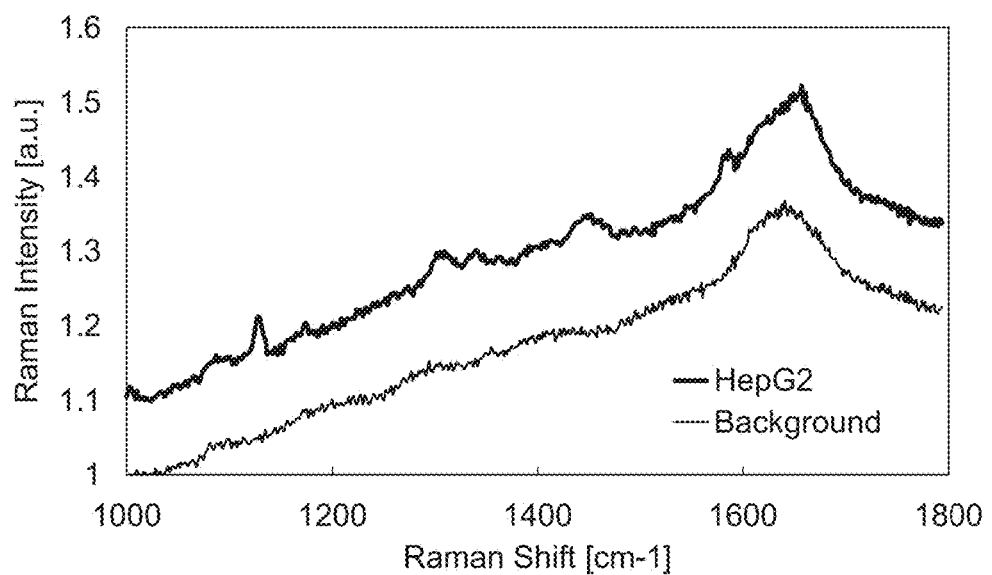
FIG. 5 shows an example of a Raman spectrum acquired by a Raman spectroscopic unit of the observation apparatus.

FIG. 5 is an example of the Raman spectrum acquired by the Raman spectroscopic unit. The observation target object in FIG. 5 is HepG2.

FIG. 5 shows a Raman spectrum of a position at which HepG2 exists in the two-dimensional spectroscopic image of the Raman scattering generated by the Raman spectroscopic unit 6, and a Raman spectrum of a position at which HepG2 does not exist (background). As shown in FIG. 5, the Raman spectrum of the position at which HepG2 exist expresses peaks that do not exist in the Raman spectrum of the position at which HepG2 do not exist. Those peaks are thought to be derived from RNA (ribo nucleic acid) or DNA (deoxyribonucleic acid) of HepG2. Also in the case where the observation target object is not HepG2, if peaks derived from RNA or DNA exist, it is possible to determine that the observation target object is a cell.

In addition to this, the detection unit 91 can detect the observation target object based on the Raman spectrum peculiar to the observation target object. The observation target object detectable by the Raman spectrum is not limited to cells and only needs to have a characteristic Raman spectrum.

In the case where the detection unit 91 identifies a characteristic spectrum in the absorption spectrum or the Raman spectrum at a specific position of the two-dimensional spectroscopic image as described above (St5: Yes), the coordinates of that position (X, Y, Z coordinates) are registered as an observation position (St6). Further, the detection unit 91 can further select whether to register the coordinates of that position depending on the size of the area in which the characteristic spectrum is identified, that is, the size of the area assumed to be the observation target object. The detection unit 91 can provide the coordinates of that position to the control unit 92.

Further, in the case where the detection unit 91 identifies no characteristic spectrum in the absorption spectrum or the Raman spectrum at that position (St5: No), that position is excluded from the observation target (St7). The detection unit 91 can confirm whether or not there is a characteristic spectrum of the absorption spectrum or the Raman spectrum in the entire area of the two-dimensional spectroscopic image, to detect the observation target object in the two-dimensional spectroscopic image.

As described above, the detection unit 91 can detect the observation target object based on the absorption spectrum acquired by the ultraviolet/visible/infrared spectroscopic unit 5 or the Raman spectrum acquired by the Raman spectroscopic unit 6. This detection result may be provided to the control unit 92 to be used for an imaging sequence by the control unit 92, or may be presented to the user.

Using the position of the observation target object provided from the detection unit 91, the control unit 92 can adjust the relative positions of the stage 2 and the microscope optical system 3 to set the field of view of the imaging unit 4 on the observation target object. Further, the control unit 92 can control the transillumination unit 7 or the imaging unit 4 and causes the imaging unit 4 to capture an image of the observation target object. This can eliminate the necessity for the user to search for the observation target object by him/herself and allows the user to easily obtain a high-magnification image of the observation target object.

[Time-Lapse Observation]

Description will be given on a time-lapse (temporal) observation using the observation apparatus 1. In the time-lapse observation, the observation target object is imaged over a long period of time and a temporal change of the observation target object is observed. Here, in the case where the observation target object is a cell or the mass of cells in a culture solution, for example, it is thought that the observation target object is moved or killed with the lapse of time. Therefore, in the case where only one spot of the observed sample is continued to be imaged, there may occur a case where the imaging is continued as it is even when the observation target object is out of the field of view or already dead and thus is not worth the observation. Here, such a problem can be solved by using the observation apparatus 1 according to this embodiment.

Figure 6:
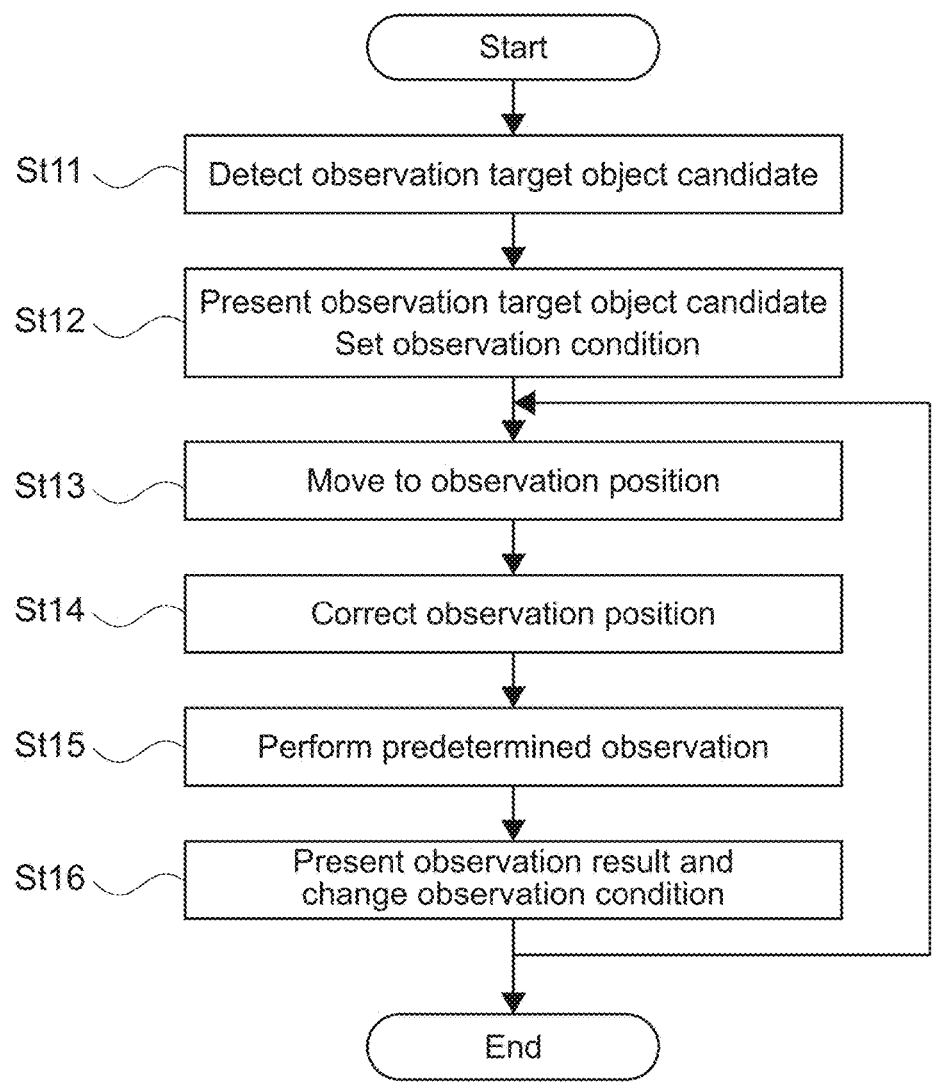
FIG. 6 is a flowchart of a time-lapse observation using the observation apparatus.

FIG. 6 is a flowchart of the time-lapse observation using the observation apparatus 1. As shown in FIG. 6, when the time-lapse observation is started, an observation target object candidate is detected (St11). As descried above, the observation target object candidate can be detected by image processing performed on the low magnification image of the observed sample.

Figure 7:
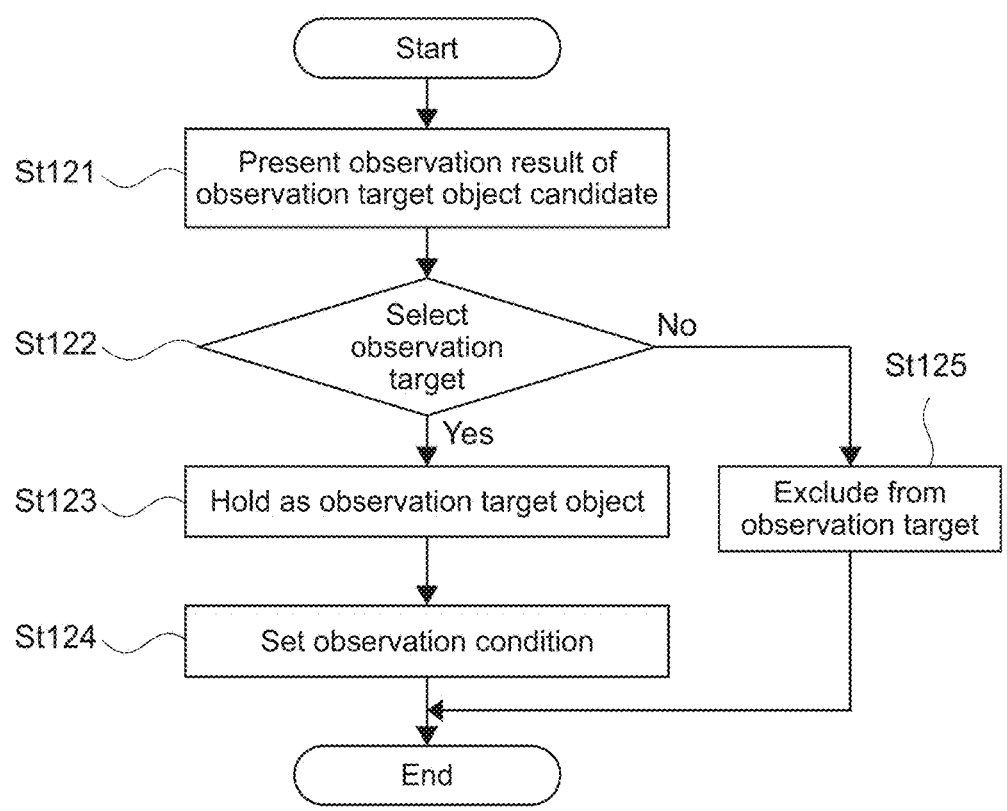
FIG. 7 is a flowchart according to the presentation of observation target object candidates and the setting of observation conditions in the time-lapse observation using the observation apparatus.

Subsequently, the presentation of observation target object candidates and the setting of observation conditions are performed (St12). FIG. 7 is a flowchart according to the presentation of observation target object candidates and the setting of observation conditions. As shown in FIG. 7, the observation results of the observation target object candidates are presented to the user (St121). The observation target object candidate is an object extracted by the image processing performed on the low magnification image of the observed sample. At this point, it is not determined whether the observation target object candidate is the observation target object or an object other than the observation target object (dust, dead cell, or the like).

Figure 8:
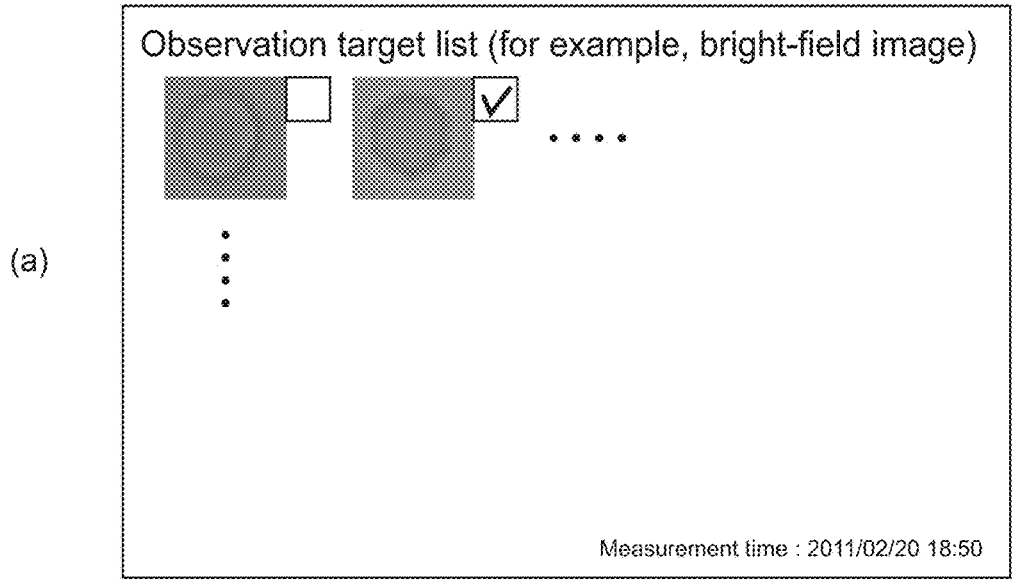
FIG. 8 are examples of observation results presented to a user by the observation apparatus.
Figure 8:
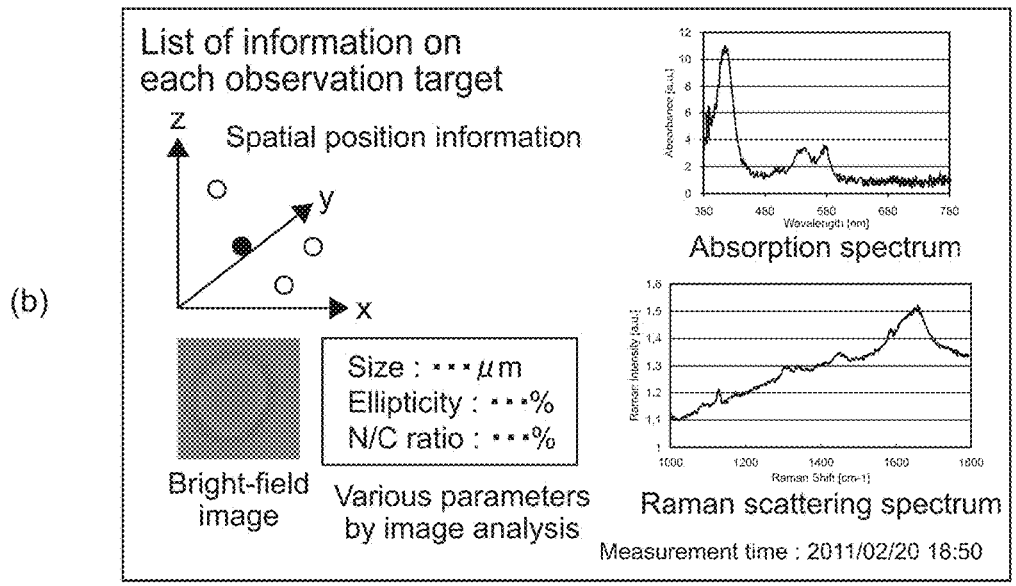

The observation apparatus 1 presents the observation results of the observation target object candidate, for example, a bright-field image, a phase difference image, an absorption spectrum, a Raman spectrum, and the like of the observation target object candidate, which are captured by the imaging unit 4, to the user. FIG. 8 are schematic diagrams each showing a display image that is displayed on the display as examples of the observation results presented to the user by the observation apparatus 1. As shown in FIG. 8(*a*), an image of the observation target object candidate (bright-field image or the like) can be trimmed for each of the observation target object candidates and displayed.

When the user selects an observation target object candidate, as shown in FIG. 8(*b*), more detailed observation results of the selected observation target object candidate can be displayed. The user can see the displayed observation results of the observation target object candidate and select, as the observation target object, an observation target object candidate to be observed.

In the case where the observation target object candidate is selected as the observation target object (St122: Yes), the observation target object candidate is held as the observation target object (St123). Subsequently, observation conditions (items to be measured, observation time intervals, and the like) are set for the observation target object (St124). On the other hand, in the case where the observation target object candidate is not selected as the observation target object (St122: No), the observation target object candidate is excluded from the observation target (St125).

Figure 9:
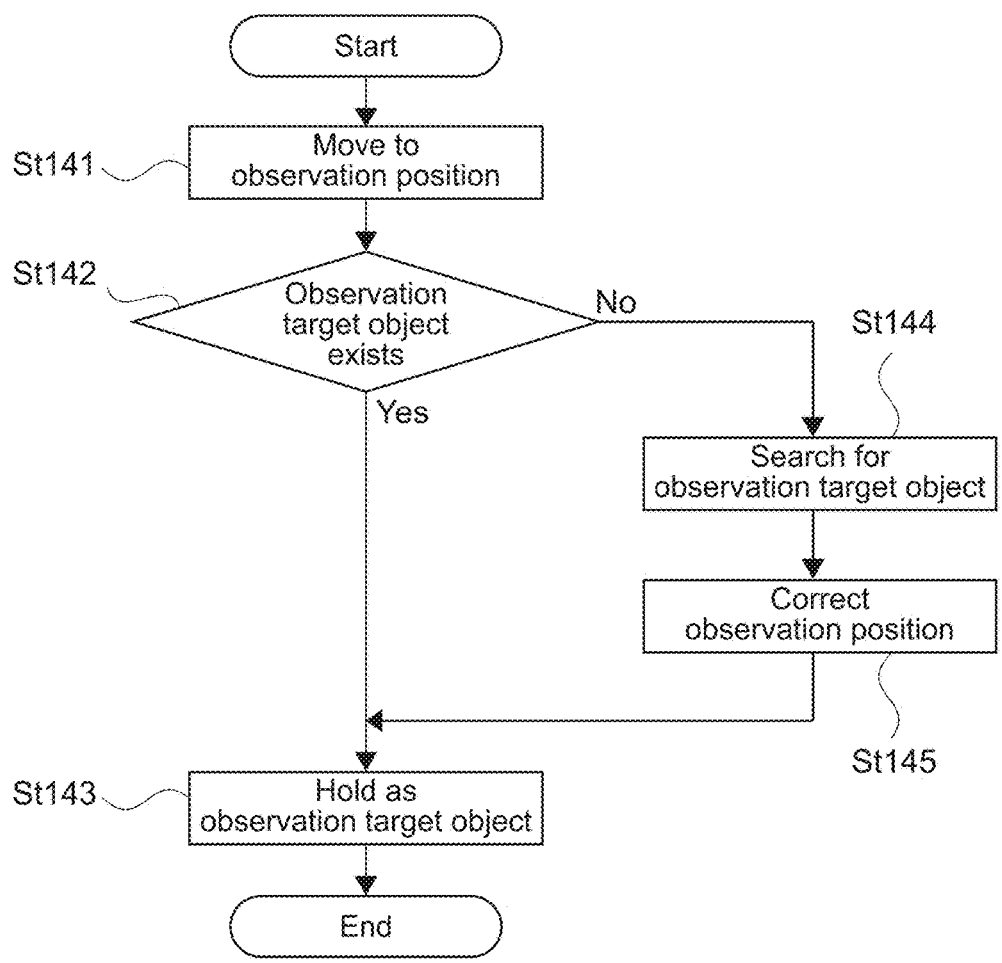
FIG. 9 is a flowchart according to the correction of an observation position in the time-lapse observation using the observation apparatus.

Referring back to FIG. 6, the field of view of the microscope optical system 3 is moved to the observation position (to the first or next observation position) (St13). Subsequently, the observation apparatus 1 corrects the observation position (St14). FIG. 9 is a flowchart according to the correction of the observation position. As shown in FIG. 9, when the field of view of the microscope optical system 3 is moved to the next observation position (St141), whether the observation target object exists or not is confirmed (St142). For example, in the case where the observation target object is a cell or the like, there is a possibility that the observation target object is moved with the lapse of time and is out of the field of view of the microscope optical system 3.

Figure 10:
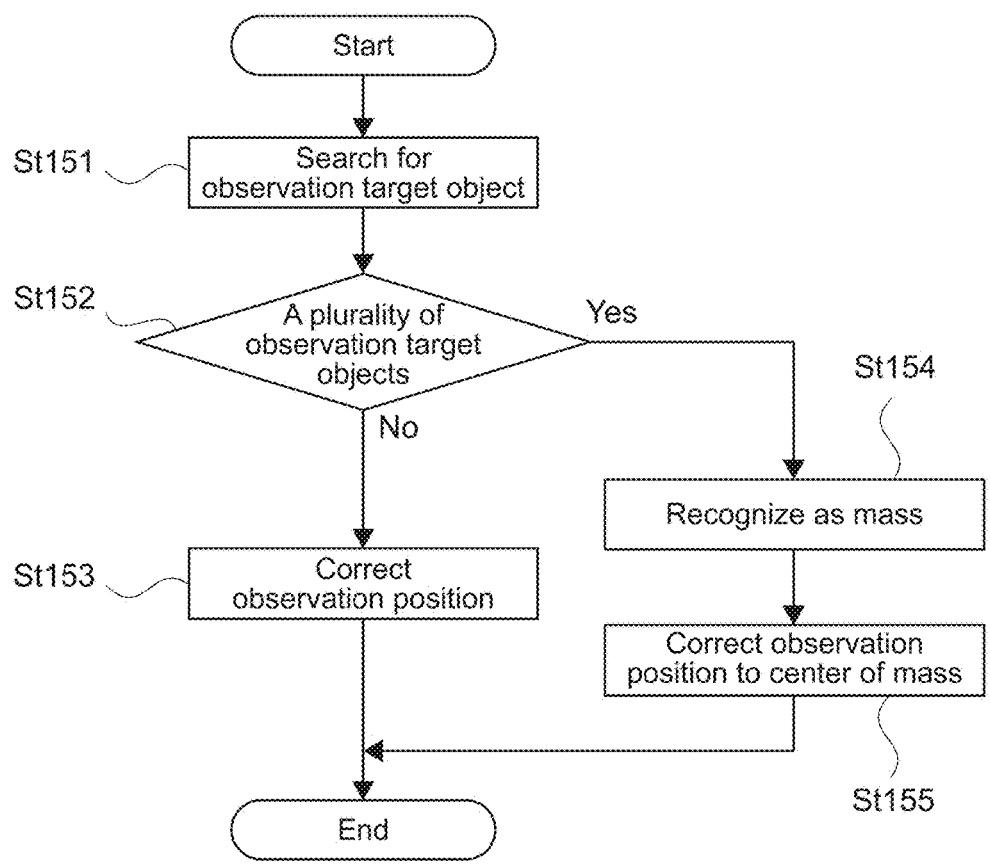
FIG. 10 is a flowchart according to the search for an observation target object in the time-lapse observation using the observation apparatus.

In the case where the observation target object exists in the field of view of the microscope optical system 3 (St142: Yes), the observation target object is held as the observation target object as it is (St143). On the other hand, in the case where the observation target object does not exist in the field of view of the microscope optical system 3 (st142: No), the observation target object is searched for (St144). FIG. 10 is a flowchart according to the search for the observation target object.

As shown in FIG. 10, the observation target object is searched for around the observation position (St151). The search of the observation target object is performed according to the flowchart shown in FIG. 2. In the case where one observation target object is detected (St152: Yes), that observation target object is regarded as the observation target object that is moved from the last observation position, and the observation position of that observation target object is corrected (St153).

On the other hand, in the case where a plurality of observation target objects are detected, the plurality of observation target objects are recognized as a mass (St154). This is because the occurrence of a cell division is assumed in the case where the observation target object is a cell. In such a case, the observation position of the observation target object is corrected to the center of the mass of observation target objects (St155).

Figure 11:
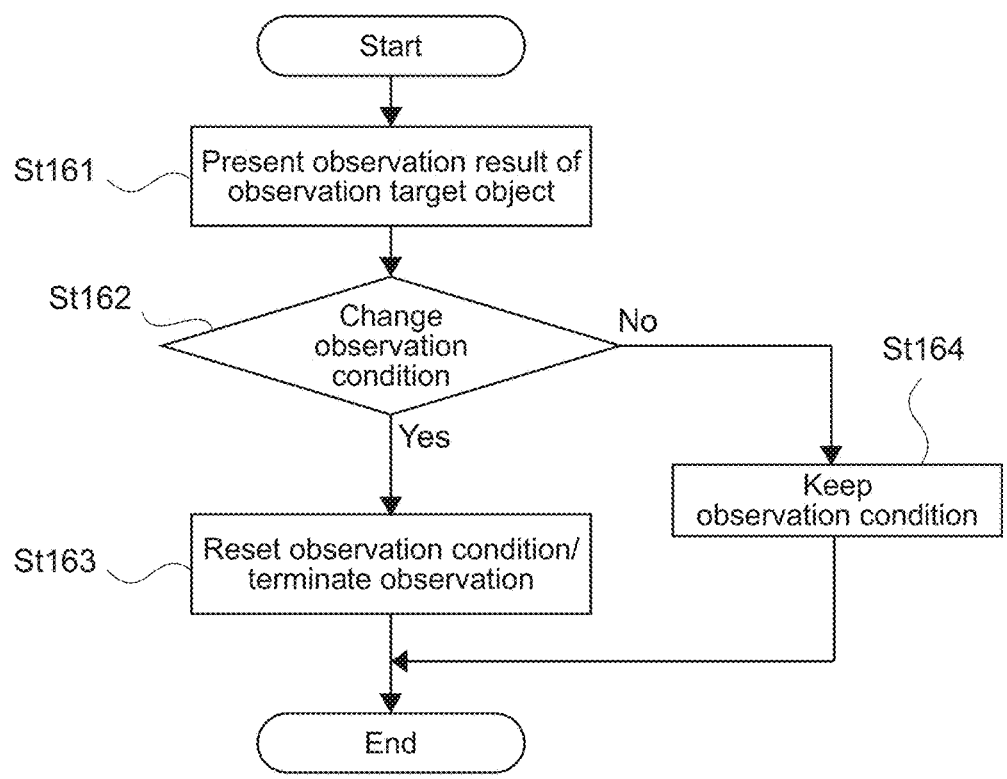
FIG. 11 is a flowchart according to the presentation of observation results and the change of the observation conditions in the time-lapse observation using the observation apparatus.

Referring back to FIG. 9, after the observation position of the observation target object is corrected as described above (St145), the observation target object is held (St143). Referring back to FIG. 6, an image of a predetermined observation, for example, a bright-field image, a phase difference image, a fluorescent image, or the like is captured (St15). Subsequently, the observation results are presented and the observation conditions are changed (St16). FIG. 11 is a flowchart according to the presentation of the observation results and the change of the observation conditions.

As shown in FIG. 11, the observation results of the observation target object are presented to the user (St161). The observation results can be presented to the user as shown in FIG. 8, for example. Subsequently, whether the observation conditions are changed or not is confirmed (St162). For the change of the observation conditions, for example, in the case where the cell as the observation target object is dead, the observation can be terminated. Further, in the case where the cell as the observation target object is undifferentiated, it is also possible to add the step of adding a medical agent (cytokine or the like) for stimulating differentiation, the step of shortening the observation time intervals, or the step of adding other items to be observed (for example, absorption spectrum).

Figure 12:
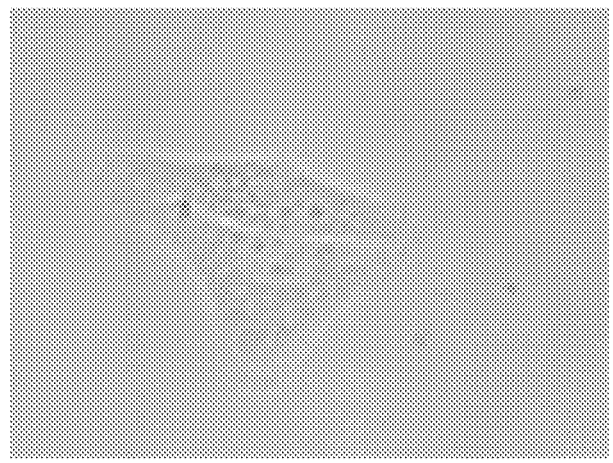
FIG. 12 are examples of images of an observation target object with different elapsed times, the images being captured by an imaging unit of the observation apparatus.
Figure 12:
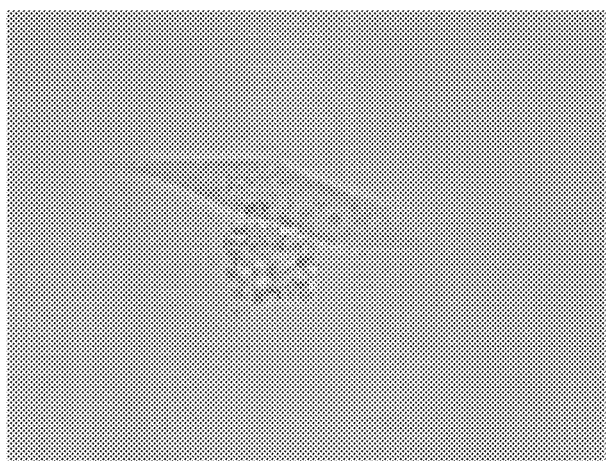

The status change of the observation target object can also be determined based on the change in size of the observation target object by using an image analysis of a bright-field image, a dark-field image, a phase difference image, and the like, in addition to the absorption spectrum or the Raman spectrum. FIG. 12 show bright-field images of the observation target object (HeLa cell) with different elapsed times. Comparing FIG. 12(a) and FIG. 12(b), it is possible to determine that a cell on the lower side is dead by the image analysis. Further, the status change of the observation target object can also be determined based on the change in refractive index anisotropy of the cell as the observation target object by the polarizing microscope image.

Further, in the case where the cell as the observation target object differentiates into specific cells, the observation can be terminated. Further, in the case where the observation target object is a cardiomyocyte, the pulsation of the cardiomyocyte can be detected by a moving image, an electric measurement, a measurement of a change in magnetic field, an ultrasonic observation, and the like. In the case where the pulsation of the cardiomyocyte reaches a standard pulsation, it is also possible to add the step of adding a medical agent, the step of shortening the observation time intervals, or the step of newly adding other items to be measured.

In the case where the observation conditions are changed (St162: Yes), the observation conditions of the observation target object are reset or the observation is terminated (St163). In the case where the observation conditions are not changed (St162: No), those observation conditions are maintained (St164).

Referring back to FIG. 6, for the next observation position, the above steps (St13 to St16) are repeatedly executed. Those steps can be performed for each predetermined period of time that is preset. As in the manner described above, the time-lapse observation is performed. As described above, the information of the observation target object can be obtained based on the absorption spectrum or the Raman spectrum of the ultraviolet, visible, or infrared area. This allows the tracking of the observation target object and allows the user to easily perform the time-lapse observation.

The present technology is not limited to the embodiment described above and can be modified without departing from the gist of the present technology.

Figure 13:
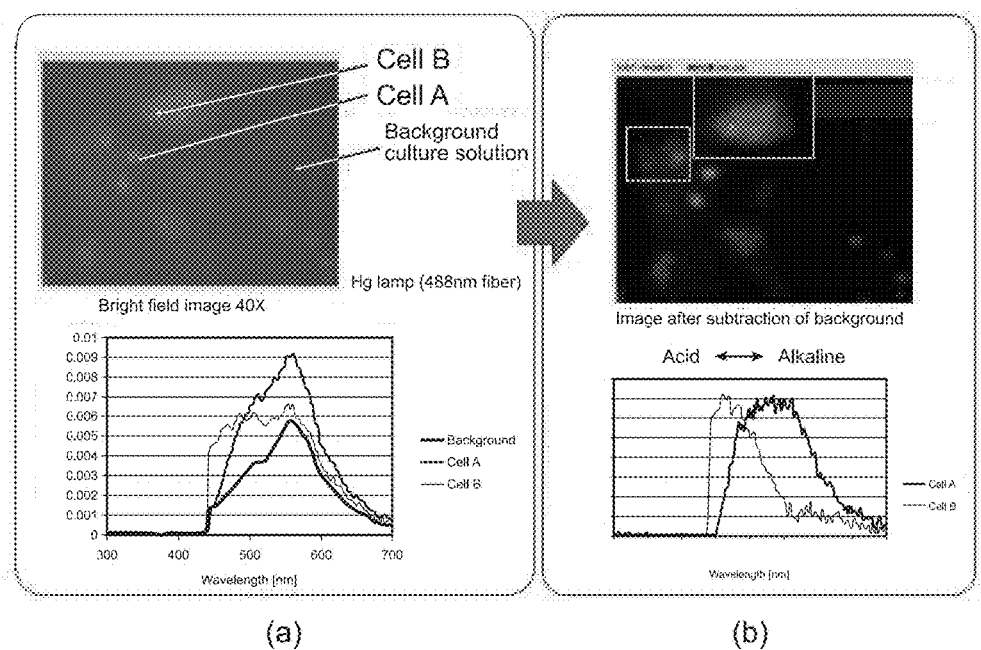
FIG. 13 are each an example of a two-dimensional spectroscopic image of fluorescence acquired by the ultraviolet/visible/infrared spectroscopic unit of the observation apparatus, and a fluorescence spectrum thereof.

In the case where the observation target object is subjected to the fluorescent labeling, the ultraviolet/visible/infrared spectroscopic unit 5 can acquire a fluorescence spectrum from the two-dimensional spectroscopic image. FIG. 13 are examples of the two-dimensional spectroscopic images of the fluorescence and examples of the fluorescence spectrum. FIG. 13(a) shows a fluorescence spectroscopic image of an observed sample obtained by loading carboxy-SNARF-1 in RC-1 (rabbit corneal epithelial cells, and a fluorescence spectrum thereof. FIG. 13(b) shows a fluorescence spectroscopic image of the same observed sample from which the background is removed, and a fluorescence spectrum thereof. As shown in those figures, in the fluorescence spectroscopic image, since the fluorescence spectrum differs depending on the presence/absence of the observation target object, the detection unit 91 can also detect the observation target object based on the fluorescence spectrum acquired by the ultraviolet/visible/infrared spectroscopic unit 5.

It should be noted that the present technology can have the following configurations.

(1) An observation apparatus, including:

a microscope optical system;

an imaging unit to capture an image via the microscope optical system;

a spectroscopic unit to acquire an absorption spectrum or a Raman spectrum in an ultraviolet, visible, or infrared area via the microscope optical system; and a detection unit to detect an observation target object in an observed sample by using the absorption spectrum or the Raman spectrum.

(2) The observation apparatus according to (1), further including a control unit to cause the imaging unit to capture an image of the observation target object detected by the detection unit.

(3) The observation apparatus according to (1) or (2), in which the detection unit detects an observation target object candidate based on an image of the observed sample, the image being captured by the imaging unit, and determines whether the observation target object candidate is the observation target object or not by using the absorption spectrum or the Raman spectrum.

(4) The observation apparatus according to any one of (1) to (3), in which the detection unit detects the observation target object for each predetermined time, and the control unit causes the imaging unit to capture an image of the observation target object detected by the detection unit for each predetermined time.

(5) The observation apparatus according to any one of (1) to (4), in which the detection unit determines a state of the observation target object based on the image captured by the imaging unit or the absorption spectrum or the Raman spectrum acquired by the spectroscopic unit, for each predetermined time, and determines whether the observation target object is an observation target or not.

(6) An observation program causing a computer to function as:

a detection unit to detect an observation target object in an observed sample by using an absorption spectrum or a Raman spectrum in an ultraviolet, visible, or infrared area, the absorption spectrum or the Raman spectrum being acquired by a spectroscopic unit via a microscope optical system; and a control unit to cause an imaging unit to capture an image of the observation target object detected by the detection unit.

(7) An observation method, including:

detecting, by a detection unit, an observation target object in an observed sample by using an absorption spectrum or a Raman spectrum in an ultraviolet, visible, or infrared area, the absorption spectrum or the Raman spectrum being acquired by a spectroscopic unit via a microscope optical system; and causing, by a control unit, an imaging unit to capture an image of the observation target object detected by the detection unit.

(8) An observation apparatus, including:

a microscope optical system;

an imaging unit to capture an image via the microscope optical system;

an ultraviolet/visible/infrared spectroscopic unit to acquire an absorption spectrum in an ultraviolet, visible, or infrared area via the microscope optical system; and a Raman spectroscopic unit to acquire a Raman spectrum via the microscope optical system.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

DESCRIPTION OF REFERENCE NUMERALS 1 observation apparatus
3 microscope optical system
4 imaging unit
5 ultraviolet/visible/infrared spectroscopic unit
6 Raman spectroscopic unit
91 detection unit
92 control unit

The invention claimed is:

1. An observation apparatus, comprising:
a microscope optical system; and
one or more circuits configured to:
  acquire one of an absorption spectrum or a Raman spectrum in an ultraviolet, visible, or infrared area via the microscope optical system;
  detect an observation target object in an observed sample based on the one of the absorption spectrum or the Raman spectrum;
  capture an image of the detected observation target object;
  determine a status change of the observation target object based on the one of the absorption spectrum or the Raman spectrum for each lapse of an observation time interval from a time at which the observation target object is detected,
  wherein the status change corresponds to at least one of change in a position of the observation target object or change in a size of the observation target object; and
  determine that observation conditions set for the observation target object are changed based on the determined status change of the observation target object,
    wherein the observation conditions comprise at least one of the detected observation target object or the observation time interval at which the status change is determined.

2. The observation apparatus according to claim 1, wherein the one or more circuits are further configured to:
  detect an observation target object candidate based on an image of the observed sample; and
  determine that the observation target object candidate is the observation target object based on the one of the absorption spectrum or the Raman spectrum.

3. The observation apparatus according to claim 1, wherein the one or more circuits are further configured to:
  detect the observation target object for the each lapse of the observation time interval; and
  capture the image of the detected observation target object for the each lapse of the observation time interval.

4. The observation apparatus according to claim 3, wherein the one or more circuits are further configured to:
  determine a state of the observation target object based on the captured image and the one of the absorption spectrum or the Raman spectrum, for the each lapse of the observation time interval; and
  determine that the observation target object is an observation target based on the determined state.

5. The observation apparatus according to claim 1, wherein the observation conditions comprise the observation time interval at which the status change is determined.

6. A non-transitory computer-readable medium having stored thereon computer executable instructions, which when executed by a computer, cause the computer to execute operations, the operations comprising:
  acquiring one of an absorption spectrum or a Raman spectrum in an ultraviolet, visible, or infrared area via a microscope optical system;
  detecting an observation target object in an observed sample based on the one of the absorption spectrum or the Raman spectrum;
  capturing an image of the detected observation target object;
  determining a status change of the observation target object based on the one of the absorption spectrum or the Raman spectrum for each lapse of an observation time interval from a time at which the observation target object is detected,
  wherein the status change corresponds to at least one of change in a position of the observation target object or change in a size of the observation target object; and
  determining that observation conditions set for the observation target object are changed based on the determined status change of the observation target object,
  wherein the observation conditions comprise at least one of the detected observation target object or the observation time interval at which the status change is determined.

7. An observation method, comprising:
  acquiring one of an absorption spectrum or a Raman spectrum in an ultraviolet, visible, or infrared area;
  detecting an observation target object in an observed sample based on the one of the absorption spectrum or the Raman spectrum;
  capturing an image of the detected observation target object;
  determining a status change of the observation target object based on the one of the absorption spectrum or the Raman spectrum for each lapse of an observation time interval from a time at which the observation target object is detected, wherein the status change corresponds to at least one of change in a position of the observation target object or change in a size of the observation target object; and determining that observation conditions set for the observation target object are changed based on the determined status change of the observation target object, wherein the observation conditions comprise at least one of the detected observation target object or the observation time interval at which the status change is determined.

8. An observation apparatus, comprising:

a microscope optical system; and one or more circuits configured to:
   acquire an absorption spectrum in an ultraviolet, visible, or infrared area via the microscope optical system;
   acquire a Raman spectrum via the microscope optical system;
   detect an observation target object in an observed sample based on one of the absorption spectrum or the Raman spectrum;
   capture an image of the detected observation target object;
   determine a status change of the observation target object based on the one of the absorption spectrum or the Raman spectrum for each lapse of an observation time interval from a time at which the observation target object is detected,
   wherein the status change corresponds to at least one of change in a position of the observation target object or change in a size of the observation target object; and
   determine that observation conditions set for the observation target object are changed based on the determined status change of the observation target object,
   wherein the observation conditions comprise at least one of the detected observation target object or the observation time interval at which the status change is determined.

9. An observation apparatus, comprising:

a microscope optical system;

an imaging unit configured to capture an image via the microscope optical system;

an ultraviolet, visible or infrared spectroscopic unit configured to acquire an absorption spectrum in an ultraviolet, visible, or infrared area via the microscope optical system;

a Raman spectroscopic unit configured to acquire a Raman spectrum via the microscope optical system; and an optical path switching system configured to sort a light from the microscope optical system to the imaging unit, the ultraviolet, visible or infrared spectroscopic unit, and the Raman spectroscopic unit at a specific proportion.

10. The observation apparatus according to claim 9, wherein the optical path switching system includes a first optical path switching unit and a second optical path switching unit, and
   wherein the first optical path switching unit is configured to cut a first wavelength band of an excitation light from the light from the microscope optical system and transmit a second wavelength band of a fluorescence toward the second optical path switching unit, and the second optical path switching unit is configured to sort the light from the first optical path switching unit to the imaging unit, the ultraviolet, visible or infrared spectroscopic unit, and the Raman spectroscopic unit at the specific proportion.

11. The observation apparatus according to claim 10, further comprising one or more circuits configured to detect an observation target object in an observed sample based on one of the absorption spectrum or the Raman spectrum.

12. The observation apparatus according to claim 11, wherein the one or more circuits are further configured to control the imaging unit to capture a first image of the detected observation target object.

13. The observation apparatus according to claim 12, wherein the one or more circuits are further configured to:
   detect the observation target object for a plurality of time instances; and
   control the imaging unit to capture the first image of the observation target object detected for each of the plurality of time instances.

14. The observation apparatus according to claim 13, wherein the one or more circuits are configured to:
   determine, for each of the plurality of time instances, a state of the observation target object based on at least one of the first image of the observation target object captured by the imaging unit or the absorption spectrum acquired by the ultraviolet, visible or infrared spectroscopic unit or the Raman spectrum acquired by the Raman spectroscopic unit; and
   determine that the observation target object is an observation target based on the state of the observation target object.

15. The observation apparatus according to claim 10, further comprising:
   one or more circuits configured to:
      detect an observation target object candidate based on a first image of an observed sample,
      wherein the imaging unit is further configured to capture the first image of the observed sample; and
      determine that the observation target object candidate is the observation target object based on the absorption spectrum or the Raman spectrum.

\* \* \* \* \*